(12) United States Patent
Haddadi

(10) Patent No.: US 10,744,244 B2
(45) Date of Patent: Aug. 18, 2020

(54) BLOOD FLOW PUMP FOR VENTRICULAR ASSISTANCE

(71) Applicant: FINEHEART, Pessac (FR)

(72) Inventor: Mohammad Haddadi, Merignac (FR)

(73) Assignee: FINEHEART, Pessac (FR)

( * ) Notice: Subject to any disclaimer, the term of this patent is extended or adjusted under 35 U.S.C. 154(b) by 138 days.

(21) Appl. No.: 15/753,134

(22) PCT Filed: Jul. 19, 2016

(86) PCT No.: PCT/EP2016/067121
§ 371 (c)(1),
(2) Date: Feb. 15, 2018

(87) PCT Pub. No.: WO2017/032510
PCT Pub. Date: Mar. 2, 2017

(65) Prior Publication Data
US 2018/0243489 A1 Aug. 30, 2018

(30) Foreign Application Priority Data

Aug. 25, 2015 (FR) .................................... 15 57893

(51) Int. Cl.
*A61M 1/10* (2006.01)
*A61M 1/12* (2006.01)
*F04D 3/02* (2006.01)
*F04D 29/18* (2006.01)
*F04D 29/54* (2006.01)

(52) U.S. Cl.
CPC .......... *A61M 1/1031* (2014.02); *A61M 1/101* (2013.01); *A61M 1/12* (2013.01);
(Continued)

(58) Field of Classification Search
CPC ...... A61M 1/10; A61M 1/101; A61M 1/1012; A61M 1/1031; A61M 1/1046; A61M 1/12;
(Continued)

(56) References Cited

U.S. PATENT DOCUMENTS 4,625,712 A * 12/1986 Wampler ............... A61M 1/102
128/DIG. 3
5,851,174 A * 12/1998 Jarvik .................. A61M 1/1031
600/16
(Continued)

FOREIGN PATENT DOCUMENTS

EP 1481698 A2 12/2004
JP H07178163 A 7/1995

OTHER PUBLICATIONS

French Search Report from French Patent Application No. 1557893, dated Jul. 7, 2016.
(Continued)

*Primary Examiner* — Igor Kershteyn
*Assistant Examiner* — Danielle M. Christensen
(74) *Attorney, Agent, or Firm* — Greer, Burns & Crain, Ltd.

(57) ABSTRACT

A pump for immersion in a fluid includes—an inductor having guide vanes to induce linear fluid flow; —a rotor with a central, flared body, this rotor being downstream of the inductor relative to the direction of fluid circulation; —a helical blade provided around the central body; this helical blade having a flared external profile and having turns with an increasing winding pitch, and the internal casing volume being complementary to the flared helical blade, —a casing around the rotor; —a diffuser having blades making the flow of fluid linear and disposed downstream of the rotor to evacuate the fluid from the rotor; and—a diffuser insert having blades and an outlet orifice with a diameter less than the inlet diameter of the diffuser insert, the blades directing the fluid from the diffuser towards the orifice to increase the orifice outlet pressure.

20 Claims, 6 Drawing Sheets

(52) U.S. Cl.
CPC ............ *A61M 1/122* (2014.02); *F04D 3/02* (2013.01); *F04D 29/183* (2013.01); *F04D 29/548* (2013.01); *A61M 2205/3365* (2013.01); *A61M 2205/8206* (2013.01); *A61M 2206/20* (2013.01)

(58) Field of Classification Search
CPC ............ A61M 1/122; A61M 2206/20; F04D 13/0606; F04D 13/066; F04D 13/068; F04D 13/08; F04D 13/086; F04D 23/003; F04D 23/005; F04D 23/00; F04D 19/046; F04D 25/02; F04D 25/064; F04D 25/0673; F04D 25/0686; F04D 29/05; F04D 29/053; F04D 29/18; F04D 29/183; F04D 29/60; F04D 29/605; F04D 29/606
See application file for complete search history.

(56) References Cited

U.S. PATENT DOCUMENTS

| | | | | |
|---|---|---|---|---|
| 6,254,359 | B1* | 7/2001 | Aber | F04D 3/02 417/356 |
| 6,692,318 | B2* | 2/2004 | McBride | B63H 11/08 415/191 |
| 7,011,620 | B1* | 3/2006 | Siess | H02K 3/47 600/16 |
| 9,726,195 | B2* | 8/2017 | Cecere | F04D 3/02 |
| 10,111,994 | B2* | 10/2018 | Wu | A61M 1/101 |
| 2005/0250975 | A1* | 11/2005 | Carrier | F04D 3/00 600/16 |
| 2014/0341726 | A1* | 11/2014 | Wu | A61M 1/101 415/199.5 |
| 2016/0279311 | A1* | 9/2016 | Cecere | F04D 3/02 |
| 2019/0125948 | A1* | 5/2019 | Stanfield | A61M 1/101 |

OTHER PUBLICATIONS

International Search Report from International Patent Application No. PCT/EP2016/067121, dated Sep. 21, 2016.

Sabersky et al., "Fluid Flow: A First Course in Fluid Mechanics, 3rd ed." (1989), Prentice Hall College Division, Chapter 13, pp. 520-545.

Stepanoff A., "Centrifugal and Axial Flow Pumps, 2nd ed." (1957), Krieger Publishing Company, Chapters 5 & 8, pp. 69-89 & 138-159.

* cited by examiner

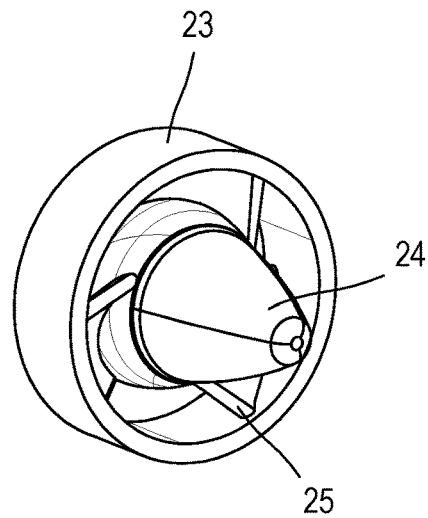
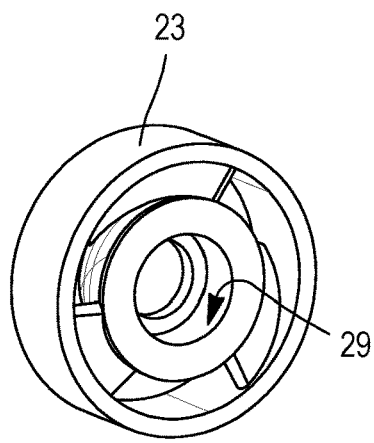
FIG. 12    FIG. 13
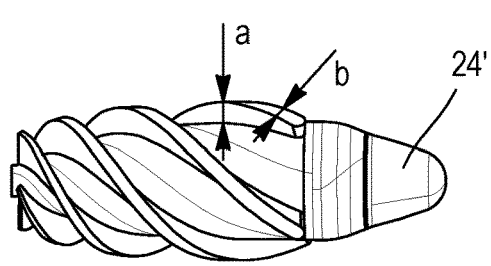
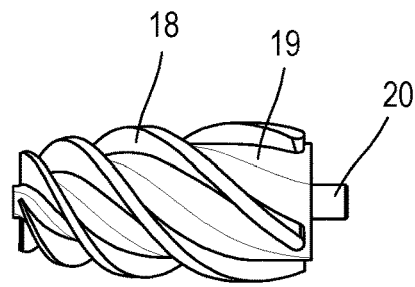
FIG. 14    FIG. 15
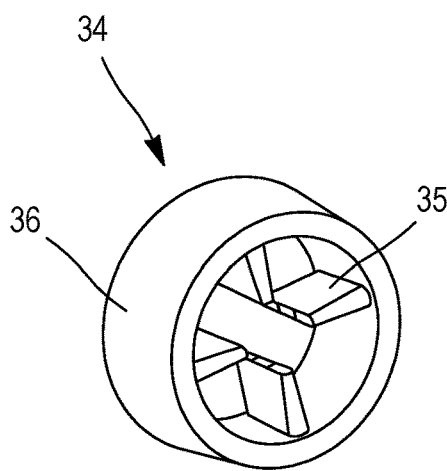
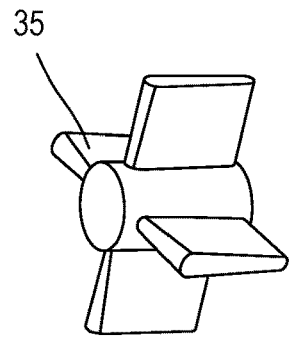
FIG. 16    FIG. 17

BLOOD FLOW PUMP FOR VENTRICULAR ASSISTANCE

BACKGROUND

The present invention relates to a ventricular assist pump. It relates for example to a pump supplied by battery and intended to be inserted into a human body in order to help blood circulation.

In the field of ventricular assist systems, two types of pump are known: the axial pump, which generates a high flow rate with a small pressure increase, and the centrifugal pump, which generates a high pressure with a low flow rate.

In order to determine which type of pump is the most suitable for a given use, it is often necessary to estimate a specific speed of the blood in the pump. The specific speed is a standardized variate calculated as a function of different parameters: the desired flow rate, the elevation height (difference in pressure between the inlet and the outlet) and the speed of rotation. Starting from this value, the pump can be chosen from the following types: centrifugal for a speed comprised between [0-1.2], mixed-flow for a specific speed comprised between [1-2.2] and axial above. Nomograms make it possible to choose a type of pump with a predefined profile for the wings or blades used in the rotor.

Regardless of the type of pump chosen, the presence of shear stress is observed in most of the pumps of the prior art, due to the fact that the rotors and casing used in the prior art create excessive vortices in the blood. Shear stress can result in hemolysis, i.e. the destruction of red blood cells. When red blood cells are destroyed, oxygen does not reach the cells, regardless of the flow rate at which the blood is conveyed.

Another drawback is the stagnation of blood causing blood clots, leading to thrombosis.

A subject of the present invention is a pump that avoids producing thrombosis.

Another subject of the invention is to avoid producing hemolysis.

SUMMARY

At least one of these aims is achieved with a pump intended to be submerged in a fluid, this pump comprising:
- an inducer equipped with guide blades to make the flow of fluid linear;
- a rotor comprising a central body having a flared shape, this rotor being intended to create kinetic energy and being arranged downstream of the inducer with respect to the direction of flow of the fluid;
- at least one helical blade produced around said central body; this helical blade having a flared external profile and comprising turns with an increasing winding pitch that tends towards infinity, the internal volume of the casing being complementary to the flared shape of said at least one helical blade;
- a casing around the rotor;
- a diffuser equipped with blades in order to make the flow of fluid linear and to increase the pressure of the fluid; this diffuser being arranged downstream of the rotor so as to evacuate the fluid outwards from the rotor, converting the kinetic energy created by the rotor into potential energy; and
- a straightener equipped with blades and an outlet orifice having a diameter less than the inlet diameter of the straightener, the blades directing the fluid originating from the diffuser to the orifice, so as to increase the speed and give the fluid a predefined profile when leaving the orifice.

In other words, the helical blade is wound around the rotor so that the angle of incidence of the helical blade decreases from the upstream end of the rotor to the downstream end; the angle of incidence being defined as the angle between the axis of rotation of the rotor and a vector at a tangent to the external surface of the helical blade. It should be noted that the blade can be wound around the rotor as principally described in the present application, but it can also be positioned on the internal wall of the casing.

The linear flow of fluid as defined here is linear by comparison with a swirling flow. This linear flow can be laminar.

The straightener according to the invention makes it possible to create a flow by concentrating the fluid so as to obtain high speed values at the outlet of the pump. In general, the vascular system of a heart has fairly high circulatory resistances. An efficient pump is a pump that is able to propel blood into the valves with sufficient pressure to overcome these circulatory resistances. The pump outlet pressure is paramount in comparison with the outlet speed, which with the pump according to the invention can reach the maximum speed of 3 m/s.

In other words, the straightener makes it possible to channel the fluid, to create a profile making it possible to have a maximum speed at a point, i.e. aligned with the aortic valve, so as to expel the flow in a laminar fashion. This makes it possible to avoid the creation of vortices at the outlet of the pump. The diameter of the outlet orifice is smaller than the inside diameter of the casing. Its small outlet diameter, for example half or a third of the inside diameter of the casing, makes it possible to adjust the pressure parameters, between 80 and 200 mmHg, and the speed parameters, between 1 and 3 m/s, while avoiding the creation of a flow with negative speed (backflow due to lack of pressure and homogeneity of the outlet flow).

The diffuser and straightener assembly according to the invention thus makes it possible for the pump to be efficient. The straightener diffuses the fluid directly to the outlet into the surrounding medium by creating a flow. This ambient medium can advantageously be said fluid, which is preferably blood.

The inducer according to the invention avoids the phenomenon of cavitation, i.e. the creation of bubbles in the fluid.

It is important to note that this pump is perfectly suitable for operating in a vertical position, or slightly slanted, i.e. inclined between 0 and 5 degrees with respect to the vertical axis. The pump according to the invention can also operate laid down like most of the pumps of the prior art.

As regards the helical blade, its external profile is flared and the internal volume of the casing is complementary to this flared shape. In most of the pumps of the prior art, the casing has a straight cylindrical internal volume so that the external profile of the blades is more or less rectangular. This is the case in particular for axial pumps where the outside diameter of the blades is identical to the inside diameter of the rectangular profile casing, which are isodiametric pumps. Such a rectangular profile design is not efficient when the pump has to be arranged vertically.

The pump according to the invention can also comprise an inlet chamber equipped with side openings so that the fluid can enter radially then engage axially towards the inducer. This inlet chamber can be cylindrical in shape comprising, on its upper part downstream of said openings, a receptacle for housing the inducer. The inlet chamber and the inducer can constitute two parts intended to be firmly fixed to one another or be designed as a single piece.

The guide blades of the inducer are advantageously designed so as to allow a rod to pass though making it possible to connect the rotor to a motor, the inducer being located between the casing and this motor. In operation, the central body (with the helical blade) rotates inside the casing without coming into contact with the other components of the pump.

According to a non-limitative embodiment, the pump comprises in total four identical helical blades uniformly distributed around the central body.

Preferably, the central body of the rotor is oblong in shape, i.e. the sides of the central body can have curves. The head of this central body can be rounded and without blades, for example in an ogive shape.

According to the invention, the diffuser can be a hollow cylinder equipped with straight guide blades distributed in its internal wall and extending from the periphery to the centre. Its role is to convert part of the kinetic energy from the fluid into pressure, this pressure being in particular transferred at the straightener. Additionally in particular, the guide blades of the diffuser can have a shape that is twisted in a direction opposite to the direction of winding of the helical blade around the central body.

According to an advantageous characteristic of the invention, when the central body comprises a rounded head without blades, the diffuser caps this rounded head, and each guide blade of the diffuser has a shape that is complementary to a facing part of the rounded head. The inside diameter of the cylinder forming the diffuser is identical to the inside diameter of the casing at the downstream end of the helical blade.

According to the invention, the straightener is arranged downstream of the diffuser in the direction of flow of the fluid. For example, the internal wall of the straightener can be conical in shape with straight guide blades arranged thereon.

According to a variant of the diffuser according to the invention, this diffuser can comprise a central part in the shape of an ogive that is pointed in the downstream direction, a cylinder around the base of the ogive, guide blades connecting this cylinder to the base of the ogive; this diffuser being intended to engage with the downstream end of the rotor via a bearing making it possible to keep the diffuser stationary with respect to the rotor. Such a diffuser makes it possible to improve the directivity, pressure and homogeneity of the outlet flow of the pump.

Similarly, in this embodiment, the guide blades of the diffuser can also be twisted in a direction opposite to the direction of winding of the helical blade around the central body. Thus, the diffuser counters the swirling nature of the fluid arriving at the rotor. After the fluid passes into the diffuser, it is fully corrected by the action of the straightener so as to constitute a laminar flow.

In particular, according to the variant, the straightener is arranged downstream of the diffuser in the direction of flow of the fluid; guide blades are straight and are designed so as to allow the head of the ogive to enter the central part of the straightener.

In general, the rotor and helical blade assembly can advantageously have a profile of centrifugal type upstream, of mixed-flow type in the central part and of axial type downstream.

With the pump according to the invention, the rotor and casing assembly has at the same time the characteristics of:

a pump of centrifugal type, i.e. radial acceleration of the fluid arriving axially; to this end, the lower part of the helical blades has a pronounced angle, of the order of 45 degrees, for example between 40 and 50 degrees, with respect to the axis of rotation of the rotor, a pump of mixed-flow type, i.e. a less pronounced slope or curve of the turns of the helical blades, and a pump of axial type, the fluid being channelled in a direction parallel to the axis of rotation of the rotor.

This configuration makes it possible to limit the shear stress which can cause hemolysis, i.e. destruction of the red blood cells. Even with a high flow rate, when red blood cells are destroyed, oxygen does not reach the cells.

Shear stress is created by the effects of blood swirling at the inlet and outlet of the pump. The pump according to the invention avoids vortices via suction of blood using a structure of the centrifugal type and an axial delivery.

According to an advantageous characteristic of the invention, the upstream part of the central body and helical blade assembly is dimensioned for a specific speed comprised between 0 and 1.2. In addition, the central part of the central body and helical blade assembly can be dimensioned for a specific speed comprised between 1 and 2.2. Finally, the central part of the central body and helical blade assembly can be dimensioned for a specific speed greater than 2.2. This is a specific speed value making it possible to classify the centrifugal, mixed-flow or axial structures respectively.

During the preliminary theoretical study before design, depending on its use and the objectives in terms of flow rate to be achieved, it was found that the pump according to the invention should have a specific speed of the order of 1. Nomograms in the technical field of the invention and commonly accepted assumptions would naturally have prompted a person skilled in the art towards a choice of a pump or a turbine of the centrifugal or axial type. However, the pump according to the invention has a very particular and innovative design in which the three types of pump are present, including the mixed-flow type. The structure of the pump according to the invention does not follow the traditional design handbook for a pump or turbine of the homogeneous type.

According to an advantageous characteristic of the invention, the pump comprises a shaft for driving and supporting the rotor, this shaft being fixed on the upstream end of the rotor and passing through the inlet chamber in its axial area. This shaft is in particular connected to a motor capable of moving the rotor.

According to the invention, the inlet chamber, the inducer, the casing and the diffuser are designed as a single piece or are firmly fixed to one another without relative movements, the rotor being held mobile in rotation in the casing.

The inducer in the inlet chamber, the diffuser and the straightener are also elements that are fixed with respect to the rotor.

Preferably, the helical blade has a radial height (its thickness in the radial direction) that is identical over its entire length (from bottom to top of the central body). In a variant, a variable radial height (its thickness in the radial direction) over its entire length can preferably be envisaged. Provision can be made for a height of 1 to 4 mm at the bottom and of 1 to 3 mm at the top of the central body, with continuous progression or in steps, depending on the pressure and speed characteristics that are required.

The overall external shape of the pump is a cylinder having a circular cross-section, but other types of cross-section can be envisaged, such as a square or triangular cross-section; the inlet chamber can have an overall shape that is different to the overall shape of the casing.

According to another aspect of the invention, provision is made for a method for driving the pump as defined above. In this method, the rotor is actuated by a motor, connected to the pump, according to the cardiac rhythm. Blood is pumped out of the pump according to the rhythm of the heartbeat, in particular of the sinusoidal type with accelerations and decelerations. The cardiac rhythm can be detected by means of a probe connecting the heart to a control unit which controls the motor.

The rotation of the pump is adapted: if the heart beats at 60 or at 120 beats per minute, the pump according to the invention follows the rhythm whereas most of the pumps of the prior art operate at a fixed speed.

BRIEF DESCRIPTION OF THE DRAWINGS

Other advantages and characteristics of the invention will become apparent on examination of the detailed description of an embodiment which is in no way limitative, and the attached diagrams, in which:

FIGS. 12 and 13 are perspective diagrammatic views of the front and rear of the diffuser according to the variant in FIGS. 11a-c, FIG. 14 is a diagrammatic view of a rotor according to a variant in which the head of the rotor is in the shape of an ogive, FIG. 15 is a diagrammatic view of a rotor according to the variant in FIGS. 11a-c, FIGS. 16 and 17 are diagrammatic views of an inducer according to the invention.

DETAILED DESCRIPTION

Figure 1:
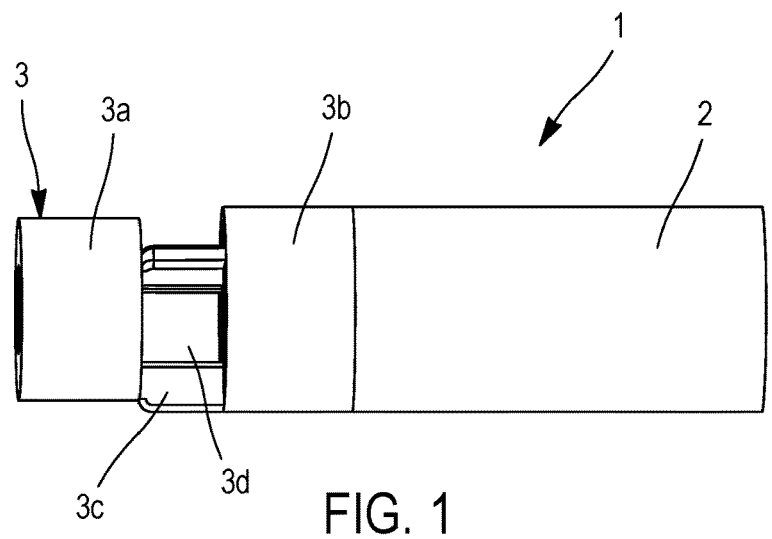
FIG. 1 is a general external view of the pump according to the invention.

In FIG. 1, the pump 1 according to the invention can be seen in the overall shape of a cylinder with a circular cross-section, intended to draw in a fluid such as blood and to deliver it so as to promote blood circulation. Such a pump is intended to be installed in a body, in particular for ventricular assistance. Its length is approximately 61.8 mm, the diameter of the casing 2 is approximately 17-20 mm, while the lower part 3a has a diameter of approximately 15-20 mm.

The pump according to the invention can advantageously, but not only, be used in a vertical position, i.e. with the casing 2 vertical and above the lower part 3a. Most pumps of the prior art are used in a horizontal mode.

According to the invention, the inlet chamber 3 serves to intake fluid, in particular blood, via inlets or openings 3d under a drawing action originating from inside the casing 2. The fluid is then delivered via an opening at the end of the casing.

Figure 5:
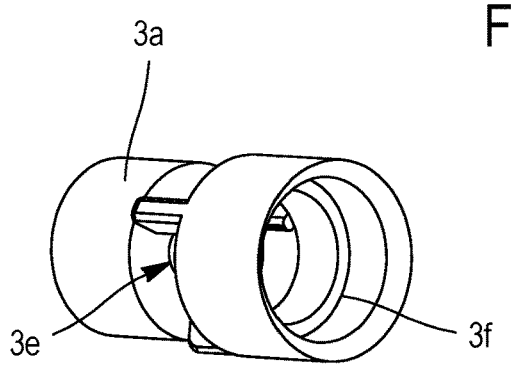
FIG. 5 is a perspective view of the inlet chamber according to the invention.

FIG. 5 shows in more detail the inlet chamber 3 constituted by a bottom part 3a, an upper part 3b, the two parts being connected by radial guides 3c delimiting openings 3d towards the inside of the inlet chamber.

The lower part 3a is a cylinder with a circular cross-section, with a thick wall so that the central part is a tunnel 3e. The diameter of the latter is less than the outside diameter of the cross-section of the cylinder, which is approximately 15 mm. In the example in FIG. 5, the diameter of the tunnel 3e is 6 mm.

The radial guides 3c are three plates inscribed in planes which intersect on the axis of the inlet chamber. The external face of each plate 3c is flush with the external lateral surface of the upper part 3b. The central area containing the axis of the inlet chamber is empty for the passage of the fluid. This central area constitutes a tunnel having a diameter greater than the diameter of the tunnel 3e.

Figure 6:
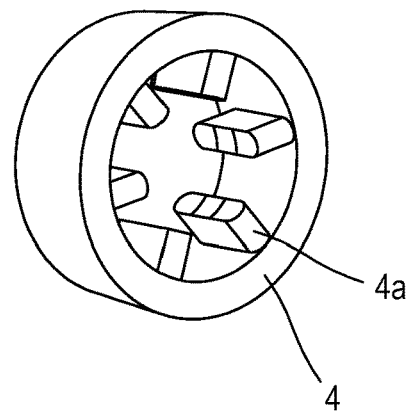
FIG. 6 is a perspective view of the inducer to be inserted into the inlet chamber according to the invention.

The upper part 3b is in the form of a cylinder having two different thicknesses, a first thickness on the upstream side, i.e. the side in contact with the radial guides 3c, and a second thickness, less than the first, on the downstream side. Between the two thicknesses is a step 3f. With such an arrangement, an inducer 4 as shown in FIG. 6 can be inserted and fixed inside the inlet chamber 3 in the thick part 3b. During insertion, this inducer 4 can rest on the ends of the guides 3c. The dimensions of the inducer 4 are such that, once inserted, its upper part is flush with the step 3f. Other embodiments can be envisaged, such as for example a single piece constituted by elements 3b and 4, or also 3 and 4. The inducer 4 is a hollow cylinder comprising radial guides 4a, for example from four to six, over the entire height of the cylinder and being inscribed in radial planes converging at the centre of the cylinder. The inducer 4 serves as a fluid inlet guide. It makes it possible to limit the cavitation in the upper stages that will be described hereinafter. The guides 4a produce a laminar flow so that the turbulent nature of the fluid is considerably reduced. This makes it possible to slow and reduce the generally rapid deterioration of the rotor which will be described below, by limiting the attacks of the fluid on the blades of this rotor.

The different parts of the pump can be contrived by moulding, 3D printing, machining or others.

Figure 2:
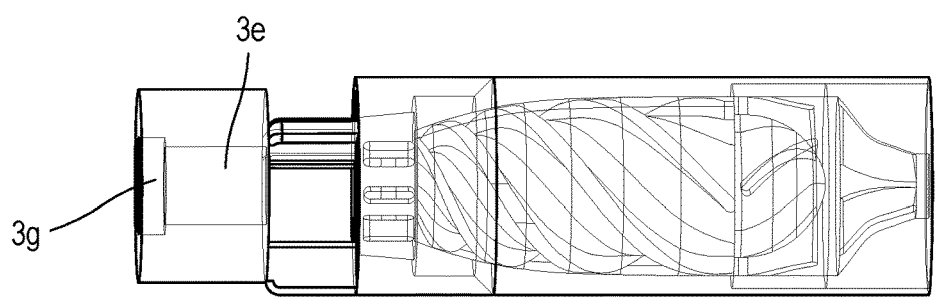
FIG. 2 is a transparent internal view of the pump according to the invention.
Figure 3:
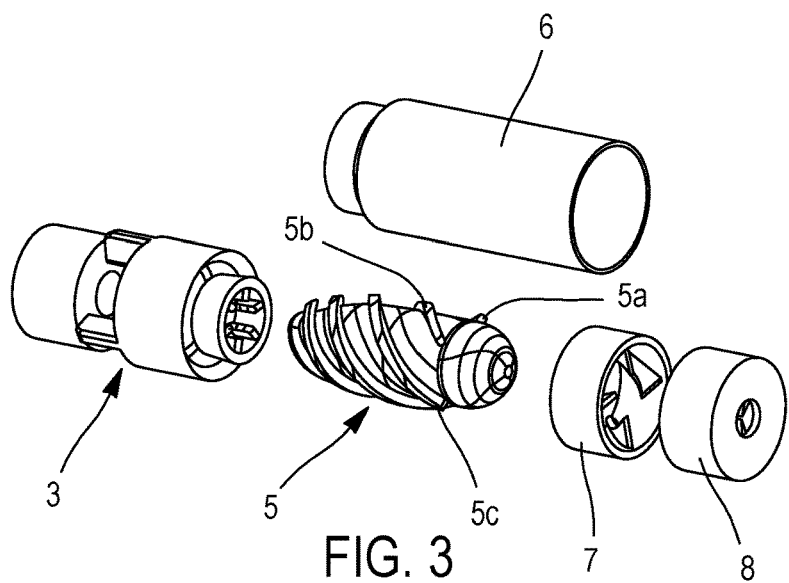
FIG. 3 is an exploded view of the pump according to the invention.

In FIGS. 2 and 3 the different parts of the pump can be seen in a transparent internal view and an exploded view. The view in FIG. 2 makes it possible to distinguish a hollow space 3g having a diameter greater than that of the tunnel 3e.

Figure 4:
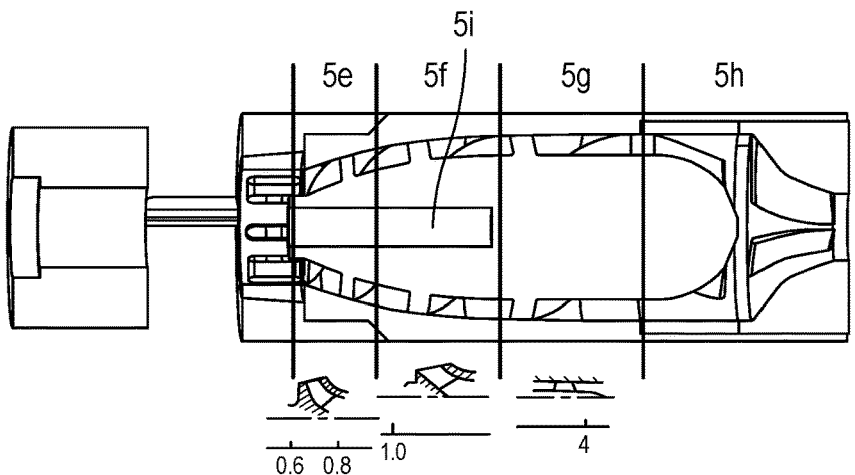
FIG. 4 is a diagrammatic longitudinal cross-section of the pump according to the invention.

The upper stages of the inlet chamber comprise a rotor 5 intended to move inside a casing 6, and outlet elements such as a diffuser 7 and a straightener 8. The rotor 5 shown in FIGS. 2, 3 and 4 has an oblong or oval shape with a single axis of symmetry: i.e. like an ogive that is elongated or stretched at one end. The rotor 5 is therefore a body the diameter of the circular cross-section (radial section) of which increases from its bottom part right up to the upper part, then decreases rapidly at the upper end. A useful part can be defined as being that for which the diameter increases. This increase is preferably continuous but not linear so that the external shape of the useful part is of a type that is conical with a convex wall.

Advantageously, between three and five blades are produced. In FIG. 2, there are four helical blades 5a, 5b, 5c, 5d, on the useful part. Each helical blade is a serpentine element having a constant or variable thickness over the entire length, so that the external shape of the rotor with the helical blades that have a developing pitch remains conical, with a convex wall. This innovative shape of the rotor 5 has a hemispherical upper part 5h and the useful part, the latter being able to be precut into three parts: a (first) lower part 5e the characteristics of which (shape, angle of incidence, pitch of the blades, etc.) are those of a centrifugal pump. In a centrifugal pump, the pumped fluid is drawn in axially then accelerated in a radial manner, and then delivered tangentially. In the present case, the fluid arrives axially via the inlet chamber then is accelerated radially due to the pronounced curvature of the base of the rotor. This pronounced curvature is obtained using nomograms known to a person skilled in the art such as nomograms published by Sabersky, Acosta and Hauptmann in 1989 ("Fluid Flow: A First Course in Fluid Mechanics", by Rolf H. Sabersky, A.3. Acosta and Edward G. Hauptmann, 3rd edition, Mar. 6, 1989, Prentice Hall College Div) or also Stepanoff A. (Stepanoff A., "Centrifugal and Axial Flow Pumps", 2nd ed. 1957, New York: Krieger Publishing Company). The centrifugal effect is optimized by the fact that the casing 6 has an internal shape that is also concave conical, complementary to the shape of the rotor 5 over the entire useful part.

The second part 5f has a mixed-flow form according to the nomograms. It is an intermediate part following the centrifugal part and having a curvature that is less pronounced than that of the centrifugal part or a plane that is inclined with respect to the axis of rotation.

Figure 8:
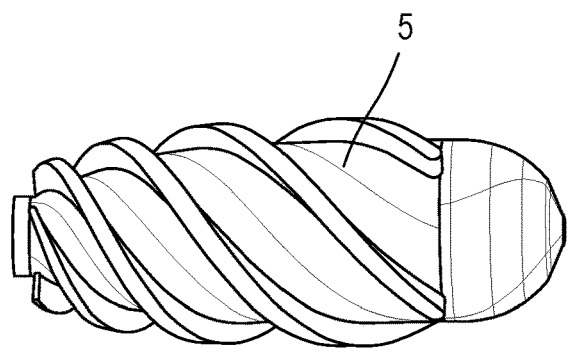
FIG. 8 is a perspective view of the rotor according to the invention.

The third part 5g has an axial form; the external shape of the rotor and the internal shape of the casing are substantially linear and parallel to the axis of rotation of the rotor. FIG. 8 shows such a rotor in detail.

Provision is made for a shaft [not shown] in the form of a fixed rod in the axis of the rotor. In operation, the shaft connects the rotor 5 to a motor [not shown], the shaft passing via the inlet chamber. In rotation, the shaft turns without coming into contact with the walls of the inlet chamber. For fixing, the shaft and the rotor can be designed as a single piece or the shaft can be inserted into the rotor 5 via the bore 5i shown in FIG. 4.

Figure 7:
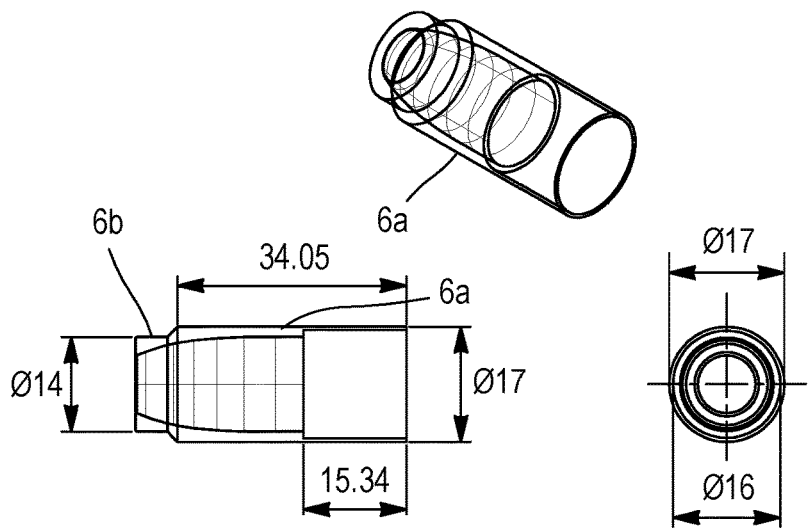
FIG. 7 is a diagram showing different views of the casing according to the invention.

FIG. 7 shows in more detail the casing 6 constituted by a main body 6a and a secondary body 6b. The main body 6a is an elongated cylinder, the secondary body being a cylinder the outside diameter of which is less than the outside diameter of the main body. The secondary body 6b is shaped so as to be inserted into and to be held therein fixed in the upper part 3b of the inlet chamber. Preferably, the bottom end of the secondary body 6b abuts the step 3f shown in FIG. 5. The internal shape of the casing 6 is complementary to the external shape of the useful part of the rotor over the entire length of the helical blades. However, an upper part of the casing has a uniform inside diameter so that it constitutes a traditional hollow cylinder with a circular cross-section. At the level of this upper part, inside the casing, the head 5h of the rotor is located, as well as the diffuser 7 and the straightener 8.

In operation, the complex internal shape of the casing makes it possible to produce centrifugal, mixed-flow and axial functions so that the fluid is drawn into the pump without creating vortices, it is then propelled to the top of the pump without shear so as not to destroy the red blood cells. The rotor according to the invention makes it possible to transmit kinetic energy to the fluid by means of its particular shape. It thus modifies the speed of the fluid without shear and also increases its pressure. To this end, the outlet elements of the pump contribute to increasing the pressure by having a reduced outlet orifice as well as specific shapes.

Figure 9:
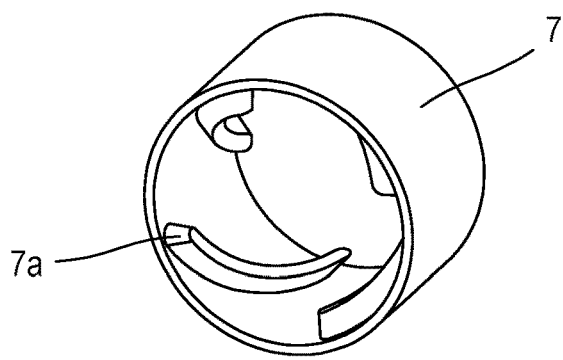
FIG. 9 is a perspective view of the diffuser according to the invention.

FIG. 9 shows the diffuser 7 which is a cylinder intended to cap the head 5h of the rotor. The diffuser comprises guide blades 7a oriented in the outflow direction of the fluid conveyed by the rotor. The orientation of the guide blades makes it possible to convert part of the kinetic energy of the fluid into pressure which is potential energy. The thickness of the guide blades can be fixed along the length of the diffuser or variable so as to conform to the shape of the head of the rotor. The height of the diffuser 7 is preferably substantially identical to that of the head of the rotor. The table below shows the properties of the diffuser:

| Diffuser | values | Tolerance Range (range of possible values) |
| --- | --- | --- |
| Length of the blade region (mm) | 6 | 3-9 |
| Number of blades | 4 | 2-5 |
| Maximum clearance gap (mm) | 0.3 | 0.1-0.5 |
| Height of the blade at the leading edge (mm) | 2 | 1-5 |
| Height of the blade at the trailing edge (mm) | 3 | 1-5 |
| theta angle at the leading edge (deg) | −2.5 | (−1)-(−40) |
| theta angle at the trailing edge (deg) | −87.5 | (−50)-(−150) |
| beta angle at the leading edge (deg) | −75 | (−15)-(−90) |
| beta angle at the trailing edge (deg) | −25 | (−1)-(−40) |
| Thickness of normal layer | 0.95 to 0.525 | 0.25-1.5 |

Figure 10:
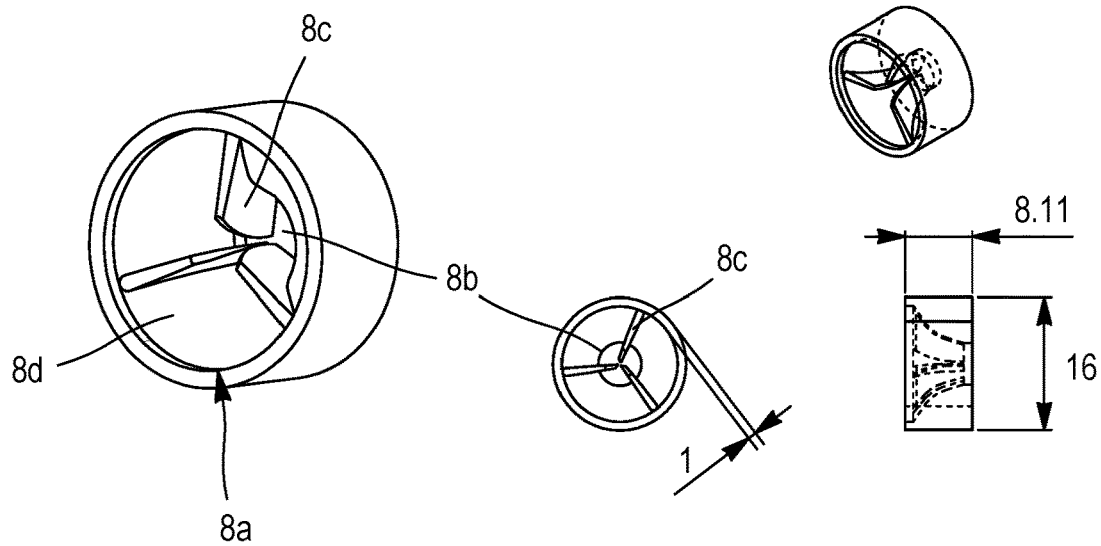
FIG. 10 is a perspective view of the straightener according to the invention.

FIG. 10 shows a straightener 8 having the role of guiding the fluid outflow, creating a laminar flow so as to eliminate turbulence. It is a cylinder 8a open at its base in order to receive the fluid originating from the rotor 5 via the diffuser 7. It comprises an orifice 8b of a smaller diameter with respect to the diameter of the opening 8a on its base.

It is possible to see an internal wall 8d, which has a concave conical shape from the opening 8a over its first half, and then a conical convex shape over its second half towards the orifice 8b. The fluid is pressurized when pushed towards the small diameter orifice.

Three guide blades 8c can also be seen, inscribed in radial planes which converge at the centre of the straightener. Each blade is a lamina the width of which is thicker at the wall than at the centre of the cylinder. The width thus decreases as the distance from the cylinder wall increases.

In the configuration described, for each guide blade, the profile on the side opposite the axis of rotation of the cylinder is curved, in particular as an arc of a circle, so that the guide blades become closer to one another at the orifice and are further away at the opening 8a.

A variant of the straightener can be designed concavely, with blades which follow the concave internal part of the straightener and the thickness of which increases linearly towards the end 8b. This variant makes it possible for the straightener to conform to the shape of the part 5h in FIG.

4 or of an ogive 24' directly fixed to the rotor in FIG. 14 or of the ogive 24 of the diffuser in FIG. 12 according to another variant.

In other words, the straightener is adapted to the shape of the head of the rotor and/or the diffuser used.

The dimensions that can be adopted are shown in the table below:

| straightener | values | Tolerance Range (range of possible values) |
|---|---|---|
| Length of the blade region (mm) | 8 | 3-9 |
| Number of blades | 3 | 2-4 |
| Maximum clearance gap (mm) | 0.3 | 0.1-0.4 |
| Height of the blade at the leading edge (mm) | 3.2 | 1-5 |
| Height of the blade at the trailing edge (mm) | 3.9 | 1-7 |
| theta angle at the leading edge (deg) | −7.65 | −1-(−30) |
| theta angle at the trailing edge (deg) | −7.45 | −1-(−30) |
| beta angle at the leading edge (deg) | −0.2 | 1-(−10) |
| beta angle at the trailing edge (deg) | 0.4 | 1-(−10) |
| Thickness of normal layer | 0.28 to 0.42 | 0.1 to 1 |

Figure 11A:
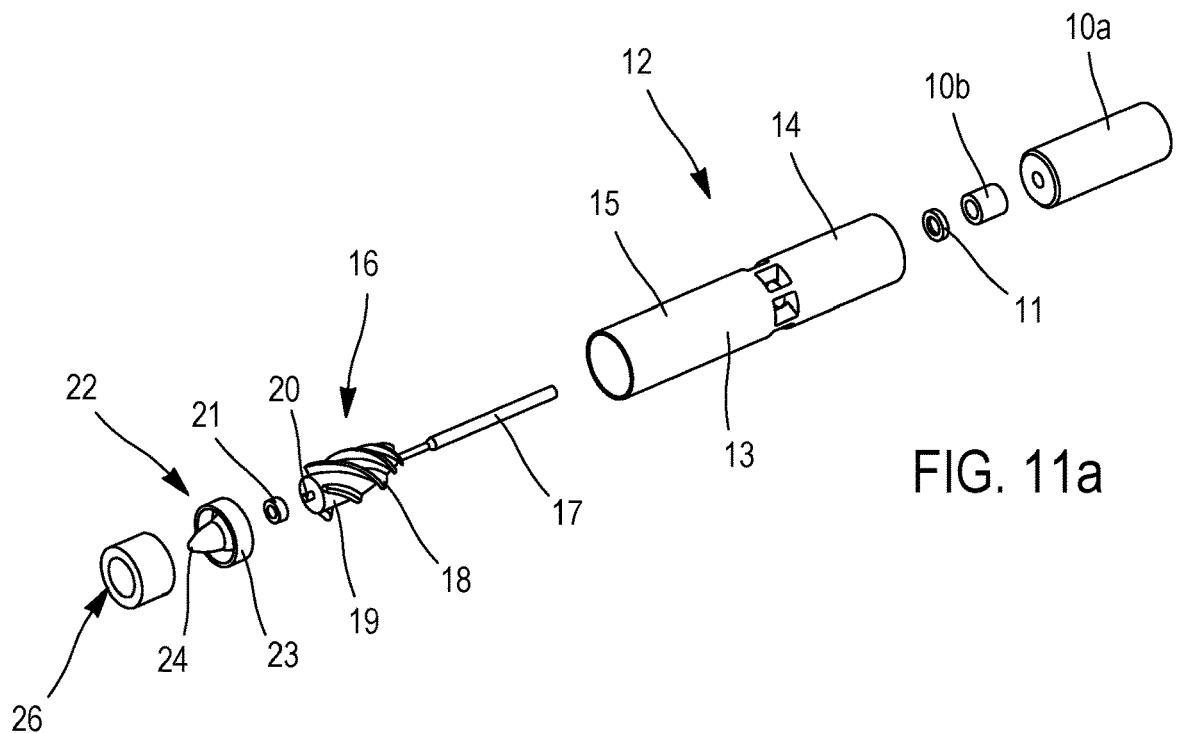
FIGS. 11a, 11b and 11c are diagrammatic views of a variant of the pump according to the invention.
Figure 11B:
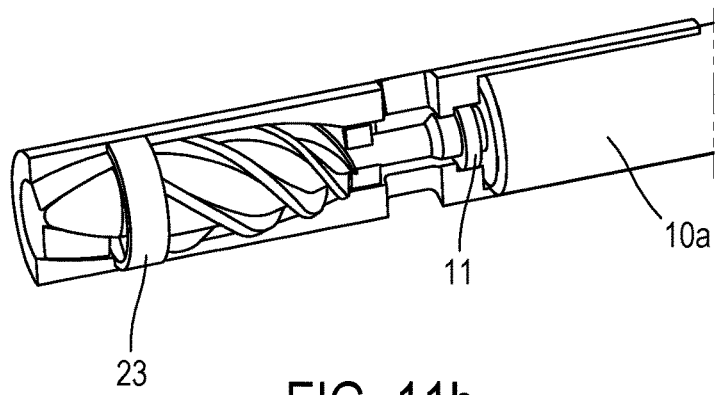
Figure 11C:
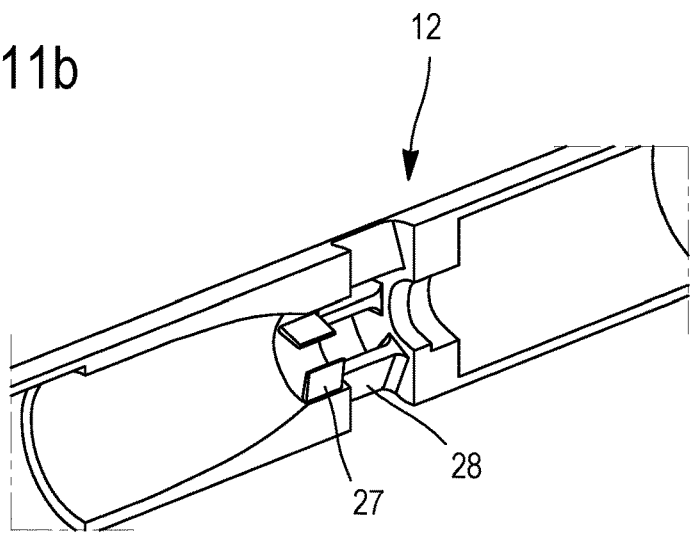

FIGS. 11*a*, 11*b* and 11*c* show a variant of the pump according to the invention. This variant is particularly suitable for efficiently diffusing blood out of the pump. The feature of this pump is its diffuser 22 arranged at the end of the active area of the rotor 16 by means of a bearing 21. This feature is shown in FIG. 11*a* together with other components of the pump, these components being different to those described in the other figures; however, the use of components that have already been described can naturally be envisaged in so far as they are compatible with the present feature.

More generally, an impeller enclosure 12 can be seen, which is a part having a cylindrical shape, equipped with lateral openings 13 for the inlet of blood. A person skilled in the art will easily understand that the impeller enclosure in fact combines the functions of the casing, the inlet chamber and the inducer previously described. This impeller enclosure 12 can be designed either as a single piece which comprises the inducer, or this enclosure can be created in two separate parts to which the inducer can be added. In other words, it can have only one piece, or three separate pieces such as the lower part 14 which comprises the part 13, the inducer and the part 15 as shown in FIGS. 5, 6 and 7. The side openings 13 make it possible to see an upper part 15 of the enclosure that is higher than a lower part 14. The upper part is hollow in order to receive the rotor 16 as well as its drive shaft 17. The latter is intended to pass through the lower part 14 via its centre as far as a motor 10*a*. In other words, the motor 10*a* holds the drive shaft 17 that passes through the entire lower part 14 as far as the rotor 16 and to which it is firmly fixed in order to drive it in rotation. The motor 10*a* can be partially or fully integrated into the end of the lower part 14, but can also be arranged externally. Provision is made for a seal 11 is inside the lower part 14 for sealing between a bearing 10*b*, the motor 10*a* and the blood. In any case, this seal 11 is situated before the part 13 and after a bearing 10*b* [not shown here] which serves as a guide for the drive shaft 17. This bearing 10*b* can be situated in the lower part 14 or in the motor 10*a*.

The upper part 15 is long enough to accommodate in addition to the rotor 16, the bearing 21, the diffuser 22 and the straightener 26, these elements being connected in series.

The rotor 16 is constituted by a flared central body 19 around which are wound four helical blades 18 over the entire length of the central body. The head of the rotor is cut flat, with only a spindle 20 protruding. FIG. 15 shows in more detail the rotor 16 according to the variant in FIGS. 11*a*, 11*b* and 11*c*. It is noted that the thickness of the blades 18 is not constant along the flared central body 19. The spindle 20 is a male rod dimensioned in order to receive the bearing 21 as female element.

The outer bearing ring 21 is tightly mounted in the housing 29 (FIG. 13) of the diffuser 22, itself fixed to the inside of the part 15 of the enclosure 12. The spindle 20 of the rotor 16 is slidably mounted in the inner bearing ring 21, thus allowing the rotor in rotation to be guided in the same way as the bearing 10*b* of the motor 10*a*.

The straightener 26 is fixed in the upper part 15 of the enclosure 12, in the same way as the diffuser 22. It is a hollow cylinder equipped with straight blades arranged radially. When the pump is fully assembled, the straightener 26 is flush with or is inset (internally) from the end of the upper part 15. The assembly with the motor has a length of less than 100 mm.

In operation, the motor 10*a* of the "brushless" type causes the assembly 16 that is composed of parts 17 to 20 to turn. Blood enters via the openings 13, then passes via an inducer (not shown) arranged inside the enclosure 12. This inducer can be in the form of several straight guide blades radially fixed to the internal wall of the enclosure 12, at the bottom of the upper part 15. Blood is drawn in by the rotor 16 and passes all around the drive shaft 17 in the form of a linear flow. The blood is then driven, while turning, by the rotor to the diffuser, which bears blades twisted in the direction opposite to the direction of the helical blades. The flow of blood then stops turning and is next straightened by passing through the straightener 26 which, through its outlet orifice, creates a high-pressure laminar flow. Provision is made for the pump to operate under immersion at a frequency ranging from 500 to 10000 rpm.

In FIGS. 11*b* and 11*c*, the inside of the impeller enclosure 12 can be seen, shaped so as to accommodate the different components. The upper part 15 comprises internally a flared shape which, without touching, conforms to the external shape of the rotor 16. The blades 27 are directly produced on the internal wall of the enclosure, thus forming an inducer at the upstream end of the upper part 15. The openings 13 are produced directly on the enclosure so that only laminas 28 inscribed in planes converging at the axis of revolution of the enclosure remain. Provision is made for the drive shaft 17 along the axis of revolution of the enclosure as can be seen in Figure 11*b*. The fluid is intended to enter radially via the openings 13 and to be driven all around the drive shaft 17 in the direction of the rotor, between the helical blades until passing through the diffuser 22. The blades of the straightener can also be produced directly on the internal wall at the downstream end of the upper part 15.

The seal 11 in FIG. 11*b* prevents the fluid from descending towards the motor 10*a*. In the example shown in FIG. 11*b*, the bearing 10*b* is integrated in the motor 10*a* which itself enters into the lower part 14. FIGS. 11*b* and 11*c* are variants in which the inducer and the straightener are produced directly in the enclosure.

The dimensions of the rotor can be as shown in the table below.

| Rotor | values | Range of possible values |
|---|---|---|
| Length of the region with helical blades (mm) | 25 | 10-35 |
| number of helical blades (mm) | 4 | 2-5 |
| gap between rotor and casing (mm) | 0.3 | 0.1-0.4 |
| Height of the blade at the leading edge of the rotor (mm) | 2.9 | 1-5 |
| Height of the blade at the trailing edge of the rotor (mm) | 2 | 1-5 |
| Beta Angle at the leading edge of the rotor (deg) | 47.5 | 10-90 |
| Beta Angle at the trailing edge of the rotor (deg) | 22 | 10-90 |
| Theta Angle at the leading edge of the rotor (deg) | 0.2 | 0-50 |
| Theta Angle at the trailing edge of the rotor (deg) | 312 | 100-360 |
| Thickness of the helical blade (mm) | 0.2-1.4 | 0.1-2 |

The angles of incidence and of outlet of blood from the rotor are such that the blood is propelled to the inlet by a centrifugal force, and is released at the outlet by an axial force, the central area of the rotor being similar to a mixed force. It is noted that the height of the helical blade (its thickness in the radial direction) can vary, for example decreasing between the bottom and the top of the rotor. Moreover, the lateral thickness of the helical blade can also vary, for example increasing between the bottom and the top of the rotor. The height "a" and the lateral thickness "b" are shown diagrammatically in FIG. 14. The same dimensions can be applied for different embodiments.

FIG. 12 shows in more detail a diffuser 22 according to the invention. It is comprised by a cylinder 23 connected to an ogive 24 by twisted blades 25. FIG. 13 shows the rear of the diffuser 22. It is noted that the ogive 24 has on its rear face the housing 29 provided to receive the bearing 21 and the spindle 20.

FIG. 14 shows another variant in which the ogive 24' is integrated and pivots with the rotor. In this case, the diffuser is constituted by a cylinder like the cylinder 23 but with twisted blades fixed to this cylinder only, and allowing the head of the ogive to pass with a marginal thickness to avoid any friction.

FIGS. 16 and 17 show a diagrammatic representation of a separate inducer 34 in FIG. 16, and a diagrammatic representation of only the blades of this inducer in FIG. 17. This inducer can be designed separately. It will then be ready to be firmly fixed in an inlet chamber. It can also be produced directly in an inlet chamber or in an impeller enclosure; in this case the blades are produced on the internal wall of the inlet chamber or of the impeller enclosure. The central area of the inducer is left free for the fluid to pass. In FIG. 17, the central area of the inducer shows the flow of fluid.

Generally, and for all of the embodiments, the blades of the inducer according to the invention are thicker upstream than downstream in the direction of movement of the fluid. The progression of the thickness can be linear, but preferably discontinuous: a linear progression until a certain thickness is reached, then the thickness remains constant over the remainder of the length of the blade. Moreover, the blades can also be thicker at the point of contact with the cylinder 36 which bears them, than at the central end. Provision is also made for an angle between the radial section of each blade and the radius of the cylinder 36 bearing the blades. The numerical data are given in the table below:

| Inducer | values | Tolerance Range (range of possible values) |
|---|---|---|
| Length of the inducer region (mm) | 4.5 | 3-8 |
| Number of inducer blades | 4 | 3-6 |
| Maximum clearance gap (mm) | 0.28 | 0.1-0.3 |
| Length of the blade region of the inducer (mm) | 2.9 | 1-5 |
| $\theta_1$ angle at the leading edge (deg) | 74.41 | 30-90 |
| $\theta_2$ angle at the trailing edge (deg) | 73.7 | 30-90 |
| $\beta_1$ angle at the leading edge (deg) | 0 | −10-30 |
| $\beta_2$ angle at the trailing edge (deg) | 1.2 | −10-30 |
| Thickness of normal layer (mm) | 035-0.95 | 0.2-1 |

Figure 20:
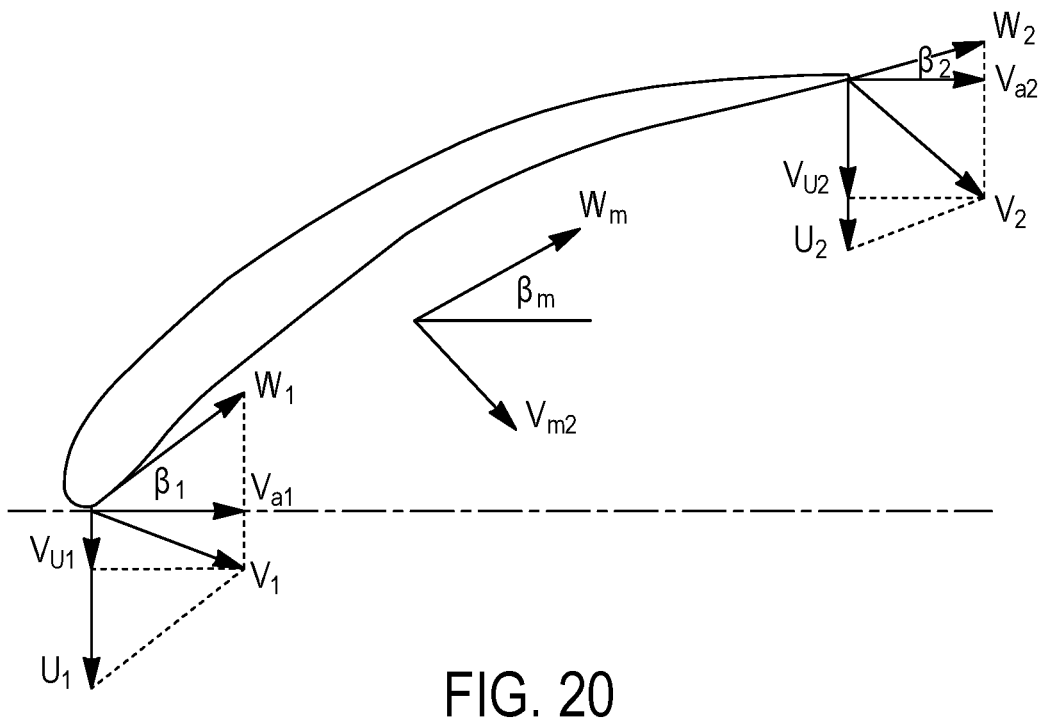
FIG. 20 is a diagrammatic cross-section of a blade with an illustration of different parameters.

FIG. 20 is a cross-section view of a blade in which different design parameters are shown. The definitions of the different parameters are shown in the figure below:

A blade 37 can be seen in which a leading edge (inlet) and a trailing edge (outlet) are shown. The following parameters make it possible to characterize a blade during the design phase:

For the inlet area:
$U_1$=speed of the blade,
$V_1$=speed of the fluid after contact with the blade (outlet speed/final speed)
$W_1$=speed of the fluid before contact with the blade (inlet speed/initial speed)
$V_{U1}$=projection of the speed vector V1 on the axis $U_1$
$V_{a1}$=Projection of $V_1$ and $W_1$ on the axis defined by the axis of the turbine
$\beta_1$=angle between the vector $W_1$ and the axis of the turbine
$\theta_1$=angle between the vector $V_1$ and the axis of the turbine For the outlet area:
$U_2$=speed of the blade,
$V_2$=speed of the fluid after contact with the blade (outlet speed/final speed)
$W_2$=speed of the fluid before contact with the blade (inlet speed/initial speed)
$V_{U2}$=projection of the speed vector $V_2$ on the axis $U_2$
$V_{a2}$=Projection of $V_2$ and $W_2$ on the axis defined by the axis of the turbine
$\theta_2$=angle between the vector $W_2$ and the axis of the turbine
$\theta_2$=angle between the vector $V_2$ and the axis of the turbine For the central area:
$V_m$=speed of the fluid after contact with the blade (outlet speed/final speed)
$W_m$=speed of the fluid before contact with the blade (inlet speed/initial speed)
$\beta_m$=angle between the vector $W_m$ and the axis of the turbine
$\theta_m$=angle between the vector $V_m$ and the axis of the turbine The sets U, V and W constitute triangles of speed of flow and serve as a reference for the definition of the speed vectors and of the angles $\beta_m$ and $\theta_m$, where m is equal to 1 for the reference point the origin of which has been shifted to the leading edge, and 2 for the reference point the origin of which has been shifted to the trailing edge. The dotted line represents the axial direction.

Figure 18:
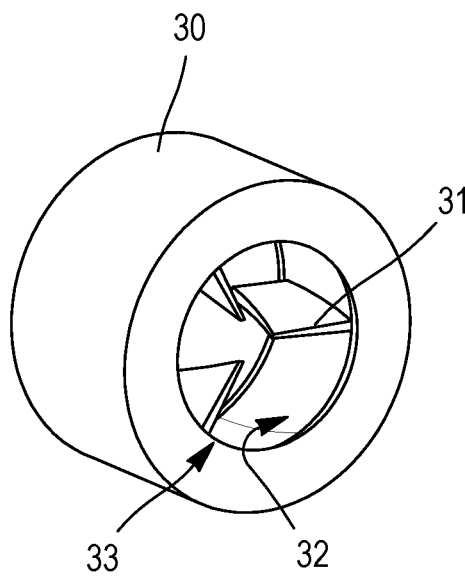
FIGS. 18 and 19 are diagrammatic views of a straightener according to the invention.
Figure 19:
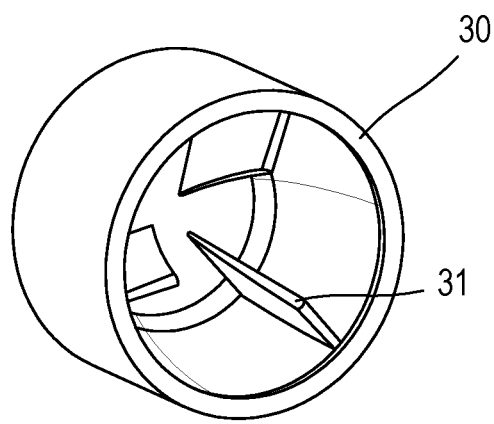

FIGS. 18 and 19 show a front view and a rear view of a straightener according to the invention. This straightener can be produced separately then fixed in the casing of the pump or produced directly on the internal wall of the casing, i.e. a wall shaped identically to the internal wall of the cylinder 30 of the straightener and the blades designed directly on this wall. The blades 31 are thicker upstream than downstream in the direction of flow of the fluid. The progression of the thickness can be linear. FIG. 18 shows the downstream side of the straightener, i.e. the point at which the fluid leaves. FIG. 19 shows the upstream side of the straightener: the fluid inlet. On this latter side, the blades 31 leave a central space that is larger than on the downstream side, the blades and the internal wall 32 of the cylinder 30 bearing the blades being designed so as to guide the fluid to the outlet orifice 33, which is narrower than the inlet of the straightener.

Of course, the invention is not limited to the examples which have just been described and numerous adjustments can be made to these examples without exceeding the scope of the invention.

The pump according to the invention can easily be implanted in a heart by its small dimension due to the fact that its particular design allows high pressure while maintaining the quality of the blood.

The pump according to the invention has a low consumption due to the fact that it operates according to the physiological cardiac rhythm: an oscillating flow.

The pump according to the invention operates by propulsion, it is a pulsed rhythm.

The pump according to the invention is advantageously intended to operate in a vertical position, the rotor being arranged vertically, the fluid enters via the inducer, passes through the rotor, then exits at the top via the diffuser and the straightener. Most pumps of the prior art operate in a horizontal position. It is the inlet and outflow capacity which allow the pump according to the invention to operate in a vertical position. Such a pump, placed in a left ventricle for example, has the advantage of having an inlet and an outlet directly in this ventricle. This makes it possible to avoid the presence of an inlet and/or outlet tube as is the case in the other devices of the prior art.

The invention claimed is:

1. A pump intended to be submerged in a fluid, the pump comprising:
    an inducer equipped with guide blades to make the flow of the fluid linear;
    a rotor comprising a central body having a flared shape and arranged downstream of the inducer with respect to the direction of flow of the fluid, said rotor configured to create kinetic energy in the fluid;
    a shaft for driving and supporting the rotor, said shaft being fixed on an upstream end of the rotor and passing through an inlet chamber;
    at least one helical blade produced around said central body of said rotor, said at least one helical blade having a flared external profile and comprising turns with an increasing winding pitch that tends towards infinity;
    a casing around the rotor, said casing defining a longitudinal axis and including an inlet and an outlet on said axis such that the fluid enters said casing and exits said casing along said axis, wherein an internal volume of said casing is complementary to the flared shape of said at least one helical blade of said rotor;
    a diffuser equipped with blades to make the flow of the fluid linear and to increase the pressure of the fluid, said diffuser being arranged downstream of the rotor so as to evacuate the fluid outwards from the rotor and convert the kinetic energy in the fluid created by the rotor into potential energy; and
    a straightener equipped with blades and an outlet orifice having a diameter that is less than the inlet diameter of the straightener, the blades of the straightener directing the fluid originating from the diffuser to the orifice so as to increase the speed and give the fluid a predefined profile when leaving the orifice.

2. The pump according to claim 1, further comprising an inlet chamber equipped with side openings so that the fluid can enter radially then engage axially towards the inducer.

3. The pump according to claim 2, wherein said inlet chamber is cylindrical in shape and comprises a receptacle for housing the inducer on an upper part downstream of said openings.

4. The pump according to claim 1, further comprising, in total, four identical helical blades uniformly distributed around the central body.

5. The pump according to claim 1, wherein the central body of the rotor is oblong in shape.

6. The pump according to claim 1, wherein the head of the central body is rounded and without blades.

7. The pump according to claim 1, wherein the diffuser is a hollow cylinder equipped with straight guide blades distributed in an internal wall of said diffuser and extending from the periphery to the center.

8. The pump according to claim 7, wherein when the central body comprises a rounded head without blades, the diffuser caps the rounded head, and each guide blade of the diffuser has a shape that is complementary to a facing part of the rounded head.

9. The pump according to claim 1, wherein the diffuser is a hollow cylinder having, distributed in an internal wall, twisted guide blades in a direction opposite to the direction of winding of the helical blade around the central body.

10. The pump according to claim 1, wherein the straightener is arranged downstream of the diffuser in the direction of flow of the fluid and includes an internal wall of the straightener that is conical in shape, and straight guide blades arranged on this internal wall.

11. The pump according to claim 1, wherein the diffuser comprises:
    a central part in the shape of an ogive that is pointed in the downstream direction;
    a cylinder around the base of the ogive;
    guide blades connecting the cylinder to the base of the ogive
    wherein the diffuser is configured to engage with the downstream end of the rotor via a bearing to keep the diffuser stationary with respect to the rotor.

12. The pump according to claim 11, wherein the guide blades of the diffuser are twisted in a direction opposite to the direction of winding of the helical blade around the central body.

13. The pump according to claim 11, wherein the straightener is arranged downstream of the diffuser in the direction of flow of the fluid and includes guide blades that are straight and designed so as to allow the head of the ogive to enter the central part of the straightener.

14. The pump according to claim 1, wherein the rotor and helical blade assembly have a profile of centrifugal type upstream, of a mixed-flow type in the central part, and of an axial type downstream.

15. The pump according to claim 1, wherein the upstream part of the central body and helical blade assembly is dimensioned for a specific speed comprised between 0 and 1.2.

16. The pump according to claim 1, wherein the central part of the central body and helical blade assembly is dimensioned for a specific speed comprised between 1 and 2.2.

17. The pump according to claim 1, wherein the central part of the central body and helical blade assembly is dimensioned for a specific speed greater than 2.2.

18. The pump according to claim 1, wherein the inlet chamber, the inducer, the casing and the diffuser are designed in a single piece or are firmly fixed to one another without relative movements, wherein the rotor is held mobile in rotation in the casing.

19. The pump according to claim 1, wherein said at least one helical blade has a radial height that is identical over the entire length of said at least one helical blade.

20. The pump according to claim 1, characterized in that said at least one helical blade has a radial height that is variable over the entire length of said at least one helical blade.

* * * * *